United States Patent [19]
Hoegnelid et al.

[11] Patent Number: 5,358,512
[45] Date of Patent: Oct. 25, 1994

[54] DEFIBRILLATOR WITH CONTROLLABLE DISCHARGE SWITCH

[75] Inventors: Kurt Hoegnelid, Västerhaninge; Kenth-Ake-Sune Nilsson, Akersberga, both of Sweden

[73] Assignee: Siemens Aktiengesellschaft, Munich, Fed. Rep. of Germany

[21] Appl. No.: 107,059

[22] Filed: Aug. 17, 1993

[30] Foreign Application Priority Data

Aug. 28, 1992 [EP] European Pat. Off. ........ 92114797.1

[51] Int. Cl.⁵ .............................................. A61N 1/39
[52] U.S. Cl. ........................................... 607/7; 607/5
[58] Field of Search ............................. 607/5, 7, 1, 2

[56] References Cited

U.S. PATENT DOCUMENTS

| 4,494,544 | 1/1985 | Lambert . |
| 4,800,883 | 1/1989 | Winstrom . |
| 5,222,492 | 6/1993 | Morgan et al. .................. 607/5 |

FOREIGN PATENT DOCUMENTS

| 0383732 | 8/1990 | European Pat. Off. . |
| 1090545 | 3/1955 | France . |
| 2156856 | 6/1973 | France . |
| 2052871 | 1/1981 | United Kingdom . |

Primary Examiner—William E. Kamm
Assistant Examiner—Kennedy J. Schaetzle
Attorney, Agent, or Firm—Hill, Steadman & Simpson

[57] ABSTRACT

Defibrillation of a heart ensues using a charging capacitor connected via a controllable switch arrangement to electrodes arranged in the region of the heart, the switch arrangement being operated to discharge across the heart tissue. In order to limit the initial current to a value not significantly exceeding the minimum value necessary to effect defibrillation, the controllable switch arrangement includes two contacts between which a contact maker, for example a mercury drop, is disposed, which is deformable under the influence of an electro-mechanical transducer. The transducer is arranged such that the contact maker connects the two contacts to one another given a prescribed excursion of the electro-mechanical transducer and, given a change of the excursion departing from the prescribed excursion, varies the electrical resistance between the contacts. The drive of the controllable switch arrangement ensues with turn-on pulses having a pulse height that is variable for setting the desired electrical resistance between the contacts.

11 Claims, 2 Drawing Sheets

FIG 4
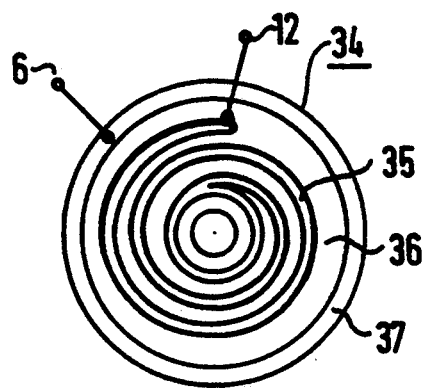
FIG 5a
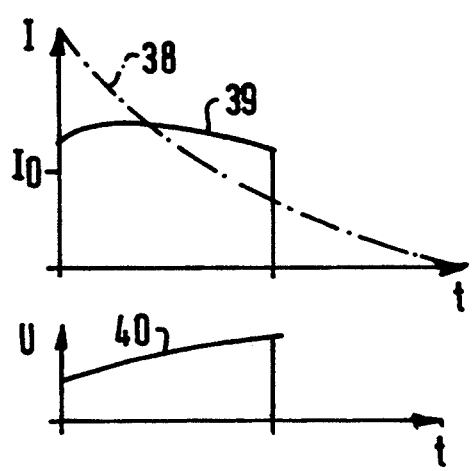
FIG 5b

DEFIBRILLATOR WITH CONTROLLABLE DISCHARGE SWITCH

BACKGROUND OF THE INVENTION

1. Field of the Invention

The present invention is directed to a defibrillator of the type having a charging capacitor that is connectable to a charging circuit by switches at both sides of the capacitor for charging and, for defibrillation of a heart, is connectable via a controllable switch means to at least two electrodes arranged in the region of the heart.

2. Description of the Prior Art and Related Subject Matter

A defibrillator of this type is disclosed in U.S. Pat. No. 4,800,883 for implantation in the body of a patient. This known defibrillator contains a charging capacitance composed of two capacitors that are connected to a charging circuit so as to be charged to a prescribed voltage. The two capacitors are also connected to two electrodes placed at the heart of the patient via a switch arrangement composed of four switches arranged in a bridge circuit. For defibrillation of the heart, the charging capacitance is first charged to a prescribed voltage and is subsequently connected via the switch means to the electrodes at the heart, so that the charging capacitance discharges across the heart tissue with a discharge current. By controlling the four switches of the switch means to open and close in pairs, the discharge current through the heart tissue is divided into a plurality of sub-currents that follow one another with alternating direction of the current.

The current through the heart tissue that produces the defibrillation is dependent on the charging voltage of the charging capacitance and on the electrical resistance of the heart tissue between the electrodes. The current has its highest value at the beginning of the discharge of the charging capacitance and then exponentially decays. In order to obtain an effective defibrillation of the heart, the current through the heart tissue must exceed a specific minimum value over a defined duration. For this reason, the charging voltage for the charging capacitance is selected such that the current is adequately high at the beginning of the charging event so that it drops below the minimum value only after the end of the defined duration. That part of the current exceeding the minimum value does not result in a more effective defibrillation (since effective defibrillation already occurs as soon as the minimum value is reached) and may lead to damage to the heart tissue due to the high initial value.

European Patent Application No. 92107996.8 discloses a defibrillator of the type initially cited, wherein a means for limiting the current for a prescribed maximum value is provided.

German OS 30 20 479 discloses a relay wherein by a defined quantity of a conductive fluid such as, for example, mercury is arranged between two contacts and is under the influence of an electro-mechanical transducer in the form of a piezoelectric drive element that can be deflected by electrical drive from a quiescent position into a working position. In the working position of the piezoelectric drive element, the liquid is deformed opposite the effect of its surface tension such that it produces a connection between the contacts.

SUMMARY OF THE INVENTION

It is an object of the present invention to prevent the occurrence of excessively high discharge currents in a defibrillator without the effectiveness of the defibrillation being thereby influenced.

This object is achieved in a defibrillator of the type initially cited with the improvement in accordance with the invention of controllable switch means, between the capacitance and the electrodes, formed by two contacts that are electrically insulated from one another and between which a contact maker is disposed that is deformable opposite the effect of an internal restorative force, such as its surface tension. An electro-mechanical transducer is arranged to act on and deform the contract maker such that the contact maker conductively connects the two contacts to one another given a prescribed excursion, of the electro-mechanical transducer and, given a change of the excursion proceeding from the prescribed excursion varies the electrical impedance between the contacts as a consequence of the change in shape dependent thereon. A control pulse generator is connected to the electro-mechanical transducer which generates the turn-on pulses with a pulse height that is variable for setting the desired electrical impedance between the contacts.

Differing from the relay disclosed by German OS 30 20 479, the current cannot only be switched on and off by the switch means given the controllable switch means of the defibrillator of the invention, but also the current amplitude can be controlled by setting the desired electrical impedance between the contacts of the controllable switch means.

In an embodiment of the defibrillator of the invention the pulse height of the turn-on pulse varies in such a way during the pulse duration that the electrical impedance between the two contacts decreases during the pulse duration. This results in the discharge current of the charging capacitor, and thus the current through the heart tissue at the beginning of the discharge event when the charging voltage of the charging capacity is highest, being limited to a value that is not harmful to the heart tissue. The electrical impedance between the two contacts can be reduced to the extent that the charging voltage of the charging capacitor decreases due to the discharge.

In the simplest case, the variation of the electrical impedance between the two contacts can be based on the changes in shape of the contact maker that are dependent on the excursion of the electro-mechanical transducer. A far better control of the electrical impedance is achieved in an embodiment wherein the contact maker covers areas of different size or different regions of the contacts given different deflected positions of the electro-magnetic transducer. The variation of the electrical impedance thereby primarily ensues due to the variation of the contact resistance between the contact maker and the contacts.

In this context, the contacts are preferably composed of a resistor material, as a result of which the degree of the change in resistance is intensified dependent on the excursion of the electro-magnetic transducer.

The contact maker is preferably composed of a prescribed quantity of a conductive liquid. Examples of such liquids are mercury, gallium, gallium alloys such as, for example, Ga—In and Ga—In—Sn, or an electrolyte. When the defibrillator of the invention is fashioned as an implantable device, it is an advantage that the melting point for the liquid can be selected comparatively high due to the body heat, so that less toxic or non-toxic substances can be employed instead of mercury.

The electro-magnetic transducer is preferably composed of a piezoelectric, electro-magnetic, magnetostrictive or electrostrictive drive elements.

DESCRIPTION OF THE DRAWINGS

FIG. 4 shows an alternative embodiment of the controllable switch.

FIGS. 5a and 5b are graphs respectively showing the output current of the defibrillator with and without current limitation on the basis of the controllable switch means and the turn-on curve for the controllable switch means of the invention.

DESCRIPTION OF THE PREFERRED EMBODIMENTS

Figure 1:
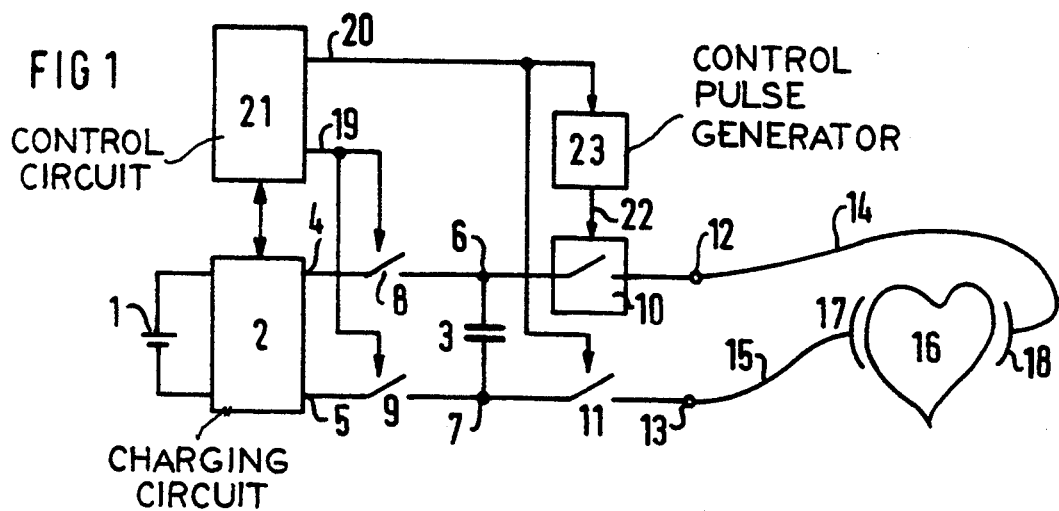
FIG. 1 is a simplified block circuit diagram of a defibrillator of the invention having a controllable switch means.

The defibrillator shown as a block circuit diagram in FIG. I contains a voltage source 1 in the form of a battery that is connected to a charging circuit 2 for a charging capacitor 3. The charging circuit 2 generates a prescribed charging voltage at its output terminals 4 and 5, the charging capacitor 3 being charged to this prescribed charging voltage when it is connected to the output terminals 4 and 5 of the charging circuit 2 at both its sides 6 and 7 via two controllable switches 8 and 9. The two sides 6 and 7 of the charging capacitor 3 are also connectable via two further switches 10 and 11 of a controllable switch means to two electrode terminals 12 and 13. Two electrodes 17 and 18 arranged in the region of the heart 16 of a patient are respectively connected via electrode lines 14 and 15 to the terminals 12 and 13. The controllable switches 8, 9 and 11 are preferably semiconductor switches, and can be driven via control outputs 19 and 20 of a control circuit 21. The switch referenced 10—whose structure shall be set forth in greater detail below with reference to FIGS. 2, 3 and 4—has a control input 22 connected to the control circuit 21 via a control pulse generator 23.

The controllable switch 10 shown in FIG. 1 includes a first, plate-shaped housing part 24 and a second, shell-shaped housing part 25 that in combination form and enclose a cavity 26. The plate-shaped housing part 24 is composed of an insulating plate 27 having an outer edge provided with an outer contact ring 28 and containing an inner contact ring 29 arranged concentrically relative thereto. The shell-shaped housing part 25 composed of metal is annularly welded onto the contact ring 28 in the region of the outer contact ring 28. The shell-shaped housing part 25 together with the outer contact ring 28 and the inner ring contact 29 form the contacts of the switch 10 and, given the defibrillator of FIG. 1, are respectively connected to the side 6 of the charging capacitor 3 and to the electrode terminal 12. The plate-shaped housing part 24 has a depression 30 in that region of the insulating plate 27 surrounded by the inner contact ring 29. The depression 30 lies opposite a corresponding depression 31 in the shell-shaped housing part 25. The two depressions 30 and 31 form a holder for a contact maker 32 that is composed of a drop of conductive liquid. The liquid is composed of a medium that does not wet the housing parts 24 and 25 such as, for example, mercury, so that it is held together in the form of a drop by its surface tension. A piezo-element 33 is applied to the upper side of the shell-shaped housing part 25, forming an electro-mechanical transducer together with the housing part 25. The piezo-element 33 is provided at both sides with contacts and terminals that form the control input 22 of the controllable switch 10.

Figure 2:
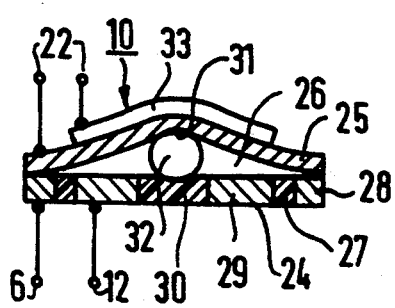
FIG. 2 is a section view of an exemplary embodiment of the controllable switch means having an electro-mechanical transducer in its quiescent position.

Given the quiescent position of the piezo-element 33 shown in FIG. 2, the drop of liquid 32 is in a stable position between the two depressions 30 and 31 without making contact with the inner contact ring 29.

Figure 3:
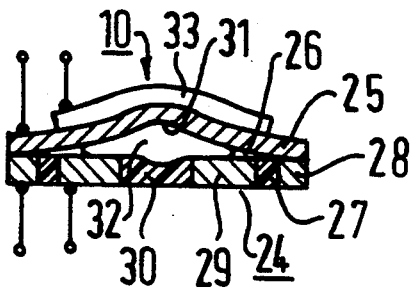
FIG. 3 shows the exemplary embodiment of FIG. 2, with the electro-mechanical transducer in a deflected position.

As FIG. 3 shows, the shell-shaped housing part 25 is deflected in the direction toward the plate-shaped housing part 24 when the piezo-element 33 is driven, causing the liquid drop 32 to be deformed against the effect of its surface tension. At a defined excursion of the piezo-element 33, or of the shell-shaped housing part 25, the liquid drop 32 comes into contact with the inner contact ring 29, so that a flow of current is possible from the side 6 of the charging capacitor 3 via the outer contact ring 28, the shell-shaped housing part 25, the liquid drop 32 and the inner contact ring 29 to the electrode terminal 12. The electrical impedance which opposes this flow of current is particularly dependent on the contact resistance between the liquid drop 32 and the inner contact ring 29. The area with which the liquid drop 32 is in contact with the inner contact ring 29 becomes larger as the shell-shaped housing part 25 is deflected farther in the direction toward the plate-housing part 24. As a result of an increasing excursion of the shell-shaped part 25, thus, the forward resistance of the controllable switch 10 can be reduced.

FIG. 4 shows an alternative embodiment 34 of the plate-shaped housing part 24 in a plan view. Instead of the inner contact ring 29 of FIGS. 2 and 3, a helical contact part 35 is set into the insulating plate 36. The helical contact part 35 is connected to the electrode terminal 12 at its location farthest from the center of the plate-shaped housing part 34. The side 6 of the charging capacitor 3 is connected to an outer contact ring 37 at the outer edge of the insulating plate 36, as in the exemplary embodiment of FIGS. 2 and 3. The line length between the outermost point of the helical contact part connected to the electrode terminal 12 and the region of the helical contact part 35 that is in communication with the liquid drop 32 becomes shorter the more the liquid drop 32 (FIGS. 2 and 3) is compressed by the shell-shaped housing part 25. The forward resistance of the switch 10 can be reduced in this way with increasing excursion of the shell-shaped housing part 25.

The discharge current of the charging capacitor 3 can be limited in the defibrillator of FIG. 1 with the assistance of the exemplary embodiments of the controllable switch 10 shown in FIGS. 2, 3, and 4. This is illustrated in FIG. 5a by two current curves 38 and 39. Current curve reference 38 occurs when the charging capacitor 3 is discharged in a conventional way, i.e. without any current limitation whatsoever, across the electrodes 17 and 18 and the heart tissue 16 lying therebetween. The current curve 38 has its highest value at the beginning of the discharge of the charging capacitor 3 and subsequently decays exponentially, whereby the minimum current $I_0$ for effective defibrillation of the heart 16 is downwardly transgressed after a certain time. As may be seen in FIG. 5a, the initial value of the current curve 38 can lie substantially above the defibrillation threshold $I_0$, at which level damage to the heart tissue 16 cannot be precluded.

By comparison, the current curve referenced 39 is obtained given drive of the controllable switch 10 with the turn-on pulse 40 shown in FIG. 5b, the current therein being limited at the start of the discharge of the charging capacitor 3 to a harmless maximum value and additionally advantageously lying above the minimum value $I_0$ required for defibrillation during a longer time span than given the current curve 38. The turn-on pulse 40 generated for this purpose by the control pulse generator 23 has an initial pulse height at the beginning of the pulse with which the controllable switch 10 is turned on. The electrical current through the switch 10 is thereby limited by the contact resistance between the liquid drop 32 and the inner contact ring 29, or the helical contact part 35. The pulse height is increased over the duration of the turn-on pulse 40, so that the electro-mechanical transducer 25 or 33 is deflected even farther as a result, and the electrical forward resistance of the controllable switch 10 is thereby reduced.

Although modifications and changes may be suggested by those skilled in the art, it is the intention of the inventors to embody within the patent warranted hereon all changes and modifications as reasonably and properly come within the scope of their contribution to the art.

We claim as our invention:

1. A defibrillator comprising:
   a capacitor;
   means for charging said capacitor with energy;
   electrode means for delivering said energy from said capacitor to a heart for defibrillating said heart;
   controllable switch means connected between said capacitor and said electrode means for selectively controlling said delivery of energy to said heart, including two normally-open electrical contacts, a contact maker disposed between said two contacts, said contact maker consisting of deformable material having a restorative force which normally maintains said contacts open, electro-mechanical transducer means disposed for acting on said contact maker given a predetermined excursion of said transducer means, for deforming said contact maker to make an electrical connection between said two contacts, and given an excursion deviating from said predetermined excursion, for varying the electrical resistance of said connection between said two contacts; and
   control pulse generator means connected to said electro-mechanical transducer means for supplying a control pulse thereto having a variable pulse height for selecting said electrical resistance between said two contacts.

2. A defibrillator as claimed in claim 1 wherein said control pulse has a pulse duration, and wherein said control pulse generator means includes means for varying said pulse height of said control pulse for reducing said electrical resistance between said two contacts over said pulse duration.

3. A defibrillator as claimed in claim 1 wherein said contact maker is deformable to cover areas of different size of said two contacts dependent on said excursion of said electro-mechanical transducer.

4. A defibrillator as claimed in claim 3 wherein said contacts consist of a resistor material.

5. A defibrillator as claimed in claim 1 wherein said contact maker is deformable to cover different regions of said contacts dependent on said excursion of said electro-mechanical transducer.

6. A defibrillator as claimed in claim 5 wherein said contacts consist of a resistor material.

7. A defibrillator as claimed in claim 1 wherein said contact maker consists of a predetermined quantity of a conductive liquid.

8. A defibrillator as claimed in claim 1 wherein said electro-mechanical transducer means comprises a drive element selected from the group consisting of piezoelectric, electro-magnetic, magnetostrictive and electrostrictive drive elements.

9. A defibrillator comprising:
   a capacitor;
   means for charging said capacitor with energy;
   electrode means for delivering said energy from said capacitor to a heart for defibrillating said heart;
   controllable switch means connected between said capacitor and said electrode means for selectively controlling said delivery of energy to said heart, including a first contact consisting of material capable of electrical conduction, a second electrode having electrically insulating regions and regions capable of electrically conducting, said first and second contacts defining a chamber therebetween, a contact maker disposed in said chamber consisting of deformable material having a restorative force which normally maintains said contact maker in an electrically insulating region of said second contact, electro-mechanical transducer means attached to one of said contacts for acting on said contact maker to deform said contact maker and bring said contact maker into contact with a region of said second contact which is capable of electrically conducting to make an electrical connection between said first and second contacts given a predetermined excursion of said transducer means, and for deforming said contact maker given an excursion deviating from said predetermined excursion for varying the electrical resistance of connection between said two contacts; and
   control pulse generator means connected to said electro-mechanical transducer means for supplying a control pulse thereto having a variable pulse height for selecting said electrical resistance between said two contacts.

10. A defibrillator as claimed in claim 9 wherein said second contact comprises a plate consisting of resistor material having a plurality of annular regions therein consisting of insulating material.

11. A defibrillator as claimed in claim 9 wherein said first contact consists of resistor material.

* * * * *